(12) United States Patent
Mirhoseini et al.

(10) Patent No.: US 11,801,093 B1
(45) Date of Patent: Oct. 31, 2023

(54) SYSTEM AND METHOD FOR TRANS MYOCARDIAL LASER REVASCULARIZATION

(71) Applicants: Mahmood Mirhoseini, Germantown, WI (US); Aria Manasheri, Germantown, WI (US)

(72) Inventors: Mahmood Mirhoseini, Germantown, WI (US); Aria Manasheri, Germantown, WI (US)

( * ) Notice: Subject to any disclaimer, the term of this patent is extended or adjusted under 35 U.S.C. 154(b) by 0 days.

(21) Appl. No.: 18/356,422

(22) Filed: Jul. 21, 2023

Related U.S. Application Data

(60) Provisional application No. 63/438,657, filed on Jan. 12, 2023.

(51) Int. Cl.
*A61B 18/24* (2006.01)
*A61B 18/00* (2006.01)

(52) U.S. Cl.
CPC .... *A61B 18/24* (2013.01); *A61B 2018/00392* (2013.01); *A61B 2018/00702* (2013.01); *A61B 2018/00761* (2013.01); *A61B 2018/00839* (2013.01)

(58) Field of Classification Search
CPC .......... A61B 18/24; A61B 2018/00392; A61B 2018/00702; A61B 2018/00761; A61B 2018/00839
USPC .......................................................... 606/12
See application file for complete search history.

*Primary Examiner* — Aaron F Roane
(74) *Attorney, Agent, or Firm* — Barry Choobin; Patent 360

(57) ABSTRACT

A system and method for transmyocardial laser revascularization (TMLR) in patients in need thereof, such as patients suffering from coronary artery disease. The system includes a Laser unit, an Electrocardiogram (EKG) unit, Vectorcardiography (VCG) unit, an Echocardiography unit, a spectrum Infrared sensor unit, and a control unit. The control unit can receive investigational data from different units and use the same to optimize the laser parameters. The Control unit can further include an AI module that can further analyze patient-related data, such as age and medical condition to further optimize the laser parameters. The laser unit can operate based on the optimized parameters to prevent unnecessary damage to the heart and allow maintaining the patency of the channels made by the laser for a longer duration.

12 Claims, 2 Drawing Sheets

SYSTEM AND METHOD FOR TRANS MYOCARDIAL LASER REVASCULARIZATION

CROSS-REFERENCE TO RELATED APPLICATIONS

This application claims priority from a U.S. Provisional patent Appl. No. 63/438,657 filed on Jan. 12, 2023, the content of which is incorporated herein by reference in its entirety.

FIELD OF INVENTION

The present invention relates to a Transmyocardial laser revascularization (TMLR) procedure, and more particularly, the present invention relates to a system and method to optimize laser parameters in the TMLR procedure.

BACKGROUND

Coronary artery diseases are one of the leading cause of death around the world. Atherosclerosis is a major cause that results in gradual build-up of plaque in the arteries narrowing down the same. This reduces the blood supply to the heart which may results in angina and heart attack. Many a times, patients with coronary artery diseases need surgery to restore the blood supply to the heart. Two main procedures currently in practice include coronary angioplasty and coronary artery bypass grafting.

Prior to the availability of coronary artery bypass surgery, in the late 1960s; researchers sought to alleviate the effects of coronary disease through a variety of techniques. Attempts were made to induce angiogenesis by performing myocardial poundage and using omentopexy to simulate the formation of myocardial blood vessels. Attempts have also been made to implant an internal mammary artery directly into the left ventricle to take advantage of the system of myocardial sinusoids and introduce oxygenated blood directly to the muscle. Other techniques designed to create conduits include boring via myocardial punch biopsy, inserting T-Tubes that connect the left ventricular cavity to the myocardium, creating myocardial incisions, and inserting polyethylene tubes.

The above experiments hypothesized that oxygen-rich blood in the left ventricle could perfuse the ischemic myocardium through the system of myocardial sinusoids and capillary circulation. Attempts were made to emulate this circulation in the mammalian heart, through needle acupuncture. Unfortunately, such channels did not stay open for more than a day or two and created scar tissue. This early work, along with the development of the first working ruby laser by Maiman in 1960, closely followed by the introduction of the carbon dioxide Laser in 1964, which led to another hypothesis that a laser could be used to create channels in the heart without damaging the tissues. The hypothesis that channels created in the left ventricle by the laser would perfuse and nourish the myocardium, remain patent and protect the muscle from ischemic changes led to the technique known as Transmyocardial laser revascularization (TMLR).

Laser techniques have been used in patients where the possibility of coronary artery bypass grafting is low. For example, in old age people, Coronary artery bypass grafting is not advised or feasible, and laser techniques have been found to effectively increase the life span in such patients. The use of laser technology has its drawbacks, the primary being damage to the heart tissue. Thus, several factors must be considered before operating on a patient using the TMLR procedure. For example, Electrocardiogram (EKG) is used in the existing laser technology to identify the electrical activity of the heart and that is considered by the surgeon to identify sites before firing the laser.

However, the risk factors with the existing laser technologies in the TMLR procedure are still significant. A need is therefore appreciated for a system and method that overcomes the said limitations in the TMLR procedure.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a system and method that has significantly higher safety in TMLR procedure.

It is another object of the present invention that unnecessary heart damage could be prevented in the TMLR procedure.

It is still another object of the present invention that process can be automated to a significant extent.

In one aspect, disclosed is a system Transmyocardial laser revascularization (TMLR) procedure on a heart of a patient, the system comprises a laser unit configured to generate a laser beam for the Transmyocardial laser revascularization (TMLR) procedure; an electrocardiogram (EKG) unit for measuring an electrical activity of the heart; a Vectorcardiography (VCG) unit for measuring an electrical activity of the heart; and a control unit operably coupled to the laser unit, the EKG unit, and the VCG unit. The control unit is configured to receive investigational data generated by the EKG unit and VCG unit, and based on the investigational data, optimize a plurality of laser parameters of the laser unit.

In one aspect, the control unit is configured to optimize the laser parameters that ensure that channels are created by the laser unit while the heart is full of blood to prevent thermal damage and maintain the patency of channels.

In one aspect, the system further comprises an echocardiography unit; and an infrared unit, wherein the control unit is operably coupled to the echocardiography unit and the infrared unit, and investigational data generated by the echocardiography unit and the infrared unit is also analyzed by the control unit in optimizing the plurality of laser parameters.

In one aspect, the plurality of laser parameters comprises angle, timing, power density, pulse duration, and wavelength.

In one aspect, an infrared spectrum generated by the infrared unit is analyzed by the control unit for synchronizing optimum parameters of the laser beam, wherein the optimum parameters of the laser beam comprise angle, power, intensity, and pulse time.

In one aspect, the control unit further comprises an AI module configured to analyze patient-related data comprising medical history and synchronize the patient-related data analysis with the investigational data analysis.

BRIEF DESCRIPTION OF THE DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

DETAILED DESCRIPTION

Figure 1:
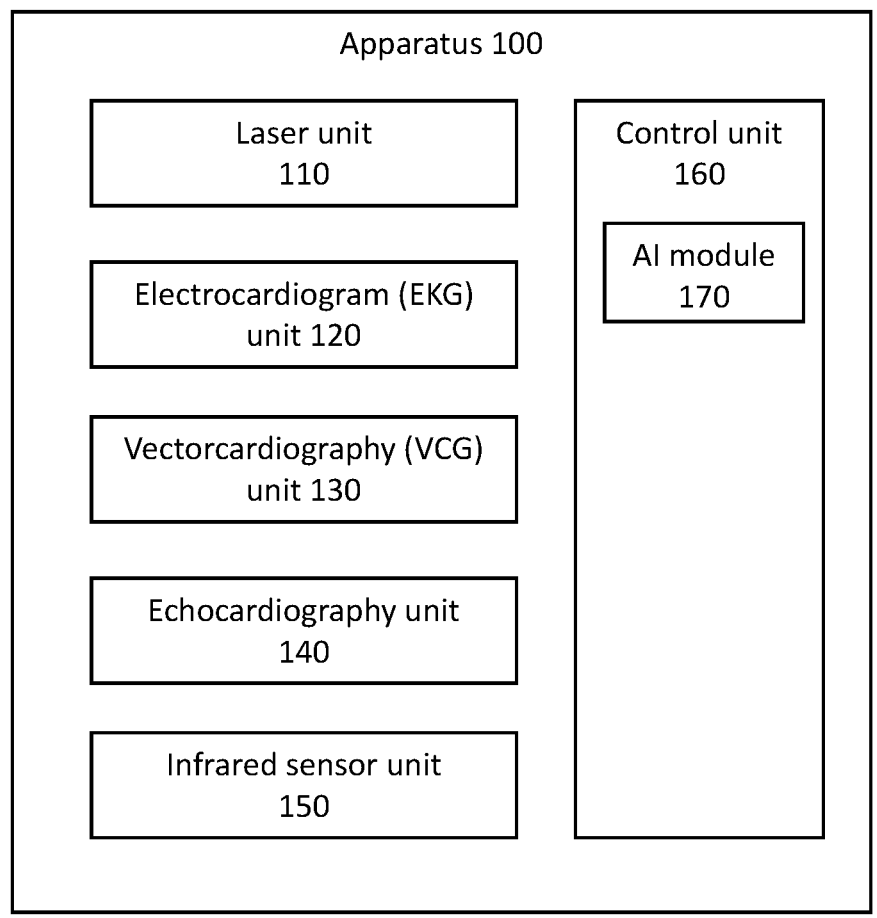
FIG. 1 is a block diagram showing an architecture of the system, according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as a system and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting to embodiments of the invention. As used herein, the singular forms "a", "an", and "the" are intended to include the plural forms as well, unless the context indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

The following detailed description is described with reference to the drawings, wherein reference numerals are used to refer to like elements throughout. In the following description, for purposes of explanation, specific details may be set forth in order to provide a thorough understanding of the subject innovation. It may be evident, however, that the claimed subject matter may be practiced without these specific details. In other instances, well-known structures and systems are shown in block diagram form to facilitate describing the subject innovation.

Disclosed are a system and method for providing transmyocardial laser revascularization (TMLR) therapy to a patient more safely and effectively. The inventors of the instant application, over the years, found that the therapy using the $CO_2$ laser with the EKG alone is not adequate, as only one form of electrical activity (diastole) is measured and that did not always coincide with the laser beam. This presents a danger of arrhythmia. Also, existing systems present a risk of thermal damage to the heart. The disclosed system and method overcome the said drawbacks with the existing TMLR procedure and provides improvements in safety and outcomes in using transmyocardial laser revascularization (TMLR) procedure in patients.

In certain implementations, the disclosed system includes a $CO_2$ laser unit, an electrocardiogram (EKG) unit, a Vectorcardiography (VCG) unit, and a control unit. The control unit is operably coupled with the laser unit, EKG unit, and VCG unit. The disclosed system may further include an echocardiography unit and an infrared sensor unit, both operably coupled to the control unit.

Disclosed is a TMLR procedure for treating patients in need thereof, such as patients suffering from coronary artery diseases. The method includes measuring the electrical activity of the heart using EKG and Vectogram. Second, in order to ensure that channels are created while the heart is full of blood to prevent thermal damage and maintain patency of channels. Also, echocardiography unit and infrared unit can also be incorporated within the system. Vectogram and echocardiogram can be used in the analysis. The control unit of the disclosed system can compute optimal timing, pulse duration, and wavelength using the input investigational data measured from the EKG unit, Vectorcardiography unit, echocardiography unit, and an infrared sensor unit. The control unit can operate the laser unit of the disclosed system to set and/or display different parameters safely and efficiently. The optimized parameter of the laser can be used in performing the TMLR procedure. Channels can be made using a cylinder shape or conical shape in smaller areas. The laser beam can be fired during diastole considering the various factors including optimal timing, pulse duration, and wavelength.

Personnel can be trained for operating the disclosed system, wherein such people can be certified for operating the disclosed system.

The use of an echocardiogram is advantageous because the blood will prevent the beam from reaching other parts of the heart, preventing unnecessary internal damage. Infrared spectrum analysis can synchronize the best parameters of the laser beam, such as angle, power, intensity, pulse time, and others.

The disclosed system can also use AI technology to further improve safety in the disclosed TMLR procedure, according to an exemplary embodiment of the present invention. Artificial intelligence (AI) and machine learning methods can be used to optimize the laser parameters using patient related data and medical history of the patient.

The inventors have over fifty years of experience in developing and then utilizing Trans Myocardial Laser Revascularization in appropriate patients. The data from various experimental procedures, training, and practice can be used as a training dataset for training the AI model. The artificial intelligence (AI) model can be trained to analyze pertinent patient data such as age, severity of angina, medications, level of physical activity, and other information. The AI can synchronize with the laser beam parameters (location, power density, duration) to guide the surgeon in safely delivering precise beams to enhance safety and prevent thermal damage. Recommended training includes certification by the Board of Laser Surgery and cooperation with those currently performing TMLR with the Advanced Laser.

It should also be noted that the precision and timing of the Laser through the use of additional measurements of realtime cardiac activity and AI, can enhance the patency of the channels. In research, it was found that channels produced hormones that prevented clotting, and long years of patency were achieved.

Referring to FIG. 1 which is a block diagram showing an architecture of the disclosed system 100. System 100 includes a Laser unit 110, an Electrocardiogram (EKG) unit 120, Vectorcardiography (VCG) unit 130, Echocardiography unit 140, and Infrared sensor unit 150. System 100 includes a control unit 160 that is operably coupled to different units. The control unit 160 can include an AI module 170.

Figure 2:
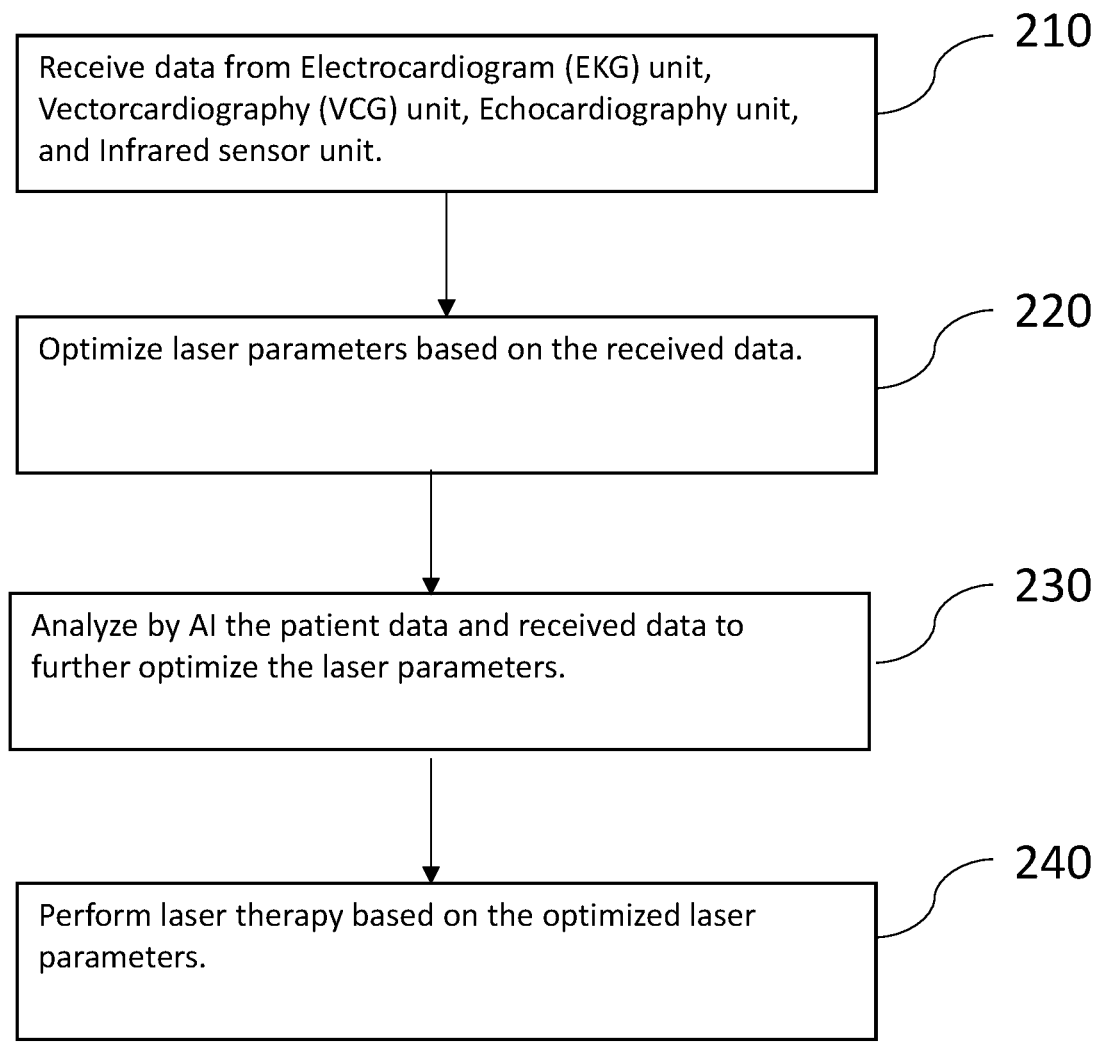
FIG. 2 is a flowchart illustrating the steps of the TMLR procedure, according to an exemplary embodiment of the present invention.

Referring to FIG. 2 shows the TMLR procedure according to an exemplary embodiment of the present invention. First, receive data from Electrocardiogram (EKG) unit, Vectorcardiography (VCG) unit, Echocardiography unit, and Infrared sensor unit, at step 210. Then optimize laser parameters based on the received data, at step 220. Analyze by AI the patient data and the received data to further optimize the laser parameters, at step 230. The disclosed system can then calculate, in near real time, the parameters of the laser for optimum laser procedure, at step 240. The optimized laser parameters can be used by a surgeon in performing the TMLR procedure. The disclosed system can assist the surgeon in delivering the best patient care and outcomes. The AI module can help incorporate subjective factors, such patient data and medical history of the patient in the analysis. The disclosed system can allow creating channels in the myocardium and endothelium that secretes immunoperoxidase, which prevents clotting and in return, supplies nourishment to the myocardium.

A system and method for transmyocardial laser revascularization (TMLR) in patients in need thereof, such as patients suffering from coronary artery disease. The system includes a Laser unit, an Electrocardiogram (EKG) unit, Vectorcardiography (VCG) unit, an Echocardiography unit, an Infrared sensor unit, and a control unit. The control unit can receive investigational data from different units and use the same to optimize the laser parameters. The Control unit can further include an AI module that can further analyze patient-related data, such as age and medical condition to further optimize the laser parameters. The laser unit can operate based on the optimized parameters to prevent unnecessary damage to the heart and allow maintaining the patency of the channels made by the laser for a longer duration.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A system Transmyocardial laser revascularization (TMLR) procedure on a heart of a patient, the system comprises:

a laser unit configured to generate a laser beam for the Transmyocardial laser revascularization (TMLR) procedure;

an electrocardiogram (EKG) unit for measuring an electrical activity of the heart;

a Vectorcardiography (VCG) unit for measuring an electrical activity of the heart; and a control unit operably coupled to the laser unit, the EKG unit, and the VCG unit, the control unit configured to:
receive investigational data generated by the EKG unit and VCG unit, and
based on the investigational data, optimize a plurality of laser parameters of the laser unit.

2. The system of claim 1, wherein the control unit is configured to optimize the laser parameters to ensure that channels are created by the laser unit while the heart is full of blood to prevent thermal damage and maintain the patency of channels.

3. The system of claim 1, wherein the system further comprises:
an echocardiography unit; and
a spectrum infrared unit,
wherein the control unit is operably coupled to the echocardiography unit and the spectrum infrared unit, and investigational data generated by the echocardiography unit and the spectrum infrared unit is also analyzed by the control unit in optimizing the plurality of laser parameters.

4. The system of claim 1, wherein the plurality of laser parameters comprises:
angle,
timing,
power density,
pulse duration, and
wavelength.

5. The system of claim 3, wherein an infrared spectrum generated by the spectrum infrared unit is analyzed by the control unit for synchronizing optimum parameters of the laser beam, wherein the optimum parameters of the laser beam comprise angle, power, intensity, and pulse time.

6. The system of claim 3, wherein the control unit further comprises an AI module configured to analyze patient-related data comprising medical history and synchronize the patient-related data analysis with the investigational data analysis.

7. A method for Transmyocardial laser revascularization (TMLR) procedure on a heart of a patient, the method comprises:
providing a system comprising:
a laser unit configured to generate a laser beam for the Transmyocardial laser revascularization (TMLR) procedure,
an electrocardiogram (EKG) unit for measuring an electrical activity of the heart,
a Vectorcardiography (VCG) unit for measuring an electrical activity of the heart, and
a control unit operably coupled to the laser unit, the EKG unit, and the VCG unit, the control unit configured to:
receive investigational data generated by the EKG unit and VCG unit, and
based on the investigational data, optimize a plurality of laser parameters of the laser unit; and
determining the plurality of laser parameters for performing the TMLR procedure using the disclosed system.

8. The method of claim 7, wherein the control unit is configured to optimize the laser parameters to ensure that channels are created by the laser unit while the heart is full of blood to prevent thermal damage and maintain the patency of channels.

9. The method of claim 7, wherein the system further comprises:
   an echocardiography unit; and
   a spectrum infrared unit,
   wherein the control unit is operably coupled to the echocardiography unit and the spectrum infrared unit, and investigational data generated by the echocardiography unit and the spectrum infrared unit is also analyzed by the control unit in optimizing the plurality of laser parameters.

10. The method of claim 7, wherein the plurality of laser parameters comprises:
    angle,
    timing,
    power density,
    pulse duration, and
    wavelength.

11. The method of claim 9, wherein an infrared spectrum generated by the spectrum infrared unit is analyzed by the control unit for synchronizing optimum parameters of the laser beam, wherein the optimum parameters of the laser beam comprise angle, power, intensity, and pulse time.

12. The method of claim 9, wherein the control unit further comprises an AI module configured to analyze patient-related data comprising medical history and synchronize the patient-related data analysis with the investigational data analysis.

* * * * *